United States Patent [19]

Gannis et al.

[11] Patent Number: 4,695,452
[45] Date of Patent: Sep. 22, 1987

[54] COSMETIC STICK

[76] Inventors: Peter M. Gannis; Aphrodite Gannis, both of 50 Kensington Rd., Stamford, Conn. 06905

[21] Appl. No.: 894,709

[22] Filed: Aug. 8, 1986

Related U.S. Application Data

[63] Continuation of Ser. No. 659,257, Oct. 10, 1984, abandoned.

[51] Int. Cl.$^4$ .................. A61K 7/42; A61K 31/355; A61K 31/375
[52] U.S. Cl. ................. 424/59; 424/DIG. 5; 424/60; 514/458; 514/474; 514/588; 514/725
[58] Field of Search ............. 424/DIG. 5, 59, 60; 514/458, 474, 588, 928, 929, 904, 969, 725

[56] References Cited

U.S. PATENT DOCUMENTS

| | | | |
|---|---|---|---|
| 2,628,930 | 2/1953 | Zentner | 514/969 |
| 3,536,816 | 10/1970 | Kellner | 514/969 |
| 3,772,446 | 11/1973 | Larsson et al. | 514/969 |
| 3,826,845 | 7/1974 | Suyama et al. | 514/969 |

FOREIGN PATENT DOCUMENTS

| | | | |
|---|---|---|---|
| 0045405 | 4/1981 | Japan | 424/DIG. 5 |
| 0120508 | 7/1982 | Japan | 424/DIG. 5 |

OTHER PUBLICATIONS

Drug & Cosmetics Industry, 5/1969, pp. 64, 68, 167 & 168, vol. 104, No. 5.

*Primary Examiner*—Dale R. Ore
*Attorney, Agent, or Firm*—Lieberman, Rudolph & Nowak

[57] ABSTRACT

A cosmetic composition of the type which is useable in the form of a cosmetic stick for applying the cosmetic composition to human skin is provided with acetylated monoglyceride in the form of a waxy solid, beeswax, and isopropyl myristate in a predetermined composition to produce a co-efficient of friction for the cosmetic composition which is greater than approximately 0.5. The cosmetic stick can be applied to the body to produce a massaging action, without causing a greasy feeling. In preferred embodiments, moisturizers such as stearic acid and cetyl alcohol are included in the composition. Additionally, emollients, such as propylene glycol, isopropyl palmitate, and dimethicone and an antioxidant formed by the synergistic combination of vitamin E and ascorbyl palmitate (Vitamin C) may also be included in the combination. Methods for preparing aqueous and nonaqueous cosmetic compositions are disclosed.

19 Claims, No Drawings

COSMETIC STICK

This application is a continuation of application Ser. No. 659257, filed 10-10-84, now abandoned.

BACKGROUND OF THE INVENTION

This invention relates generally to cosmetic stick compounds which are applied to a human body, and more particularly, to a compound which is prepared in the form of a stick so as to have a predeterminable frictional drag which produces a massaging action upon application to the skin of the human being, while simultaneously applying selectable combinations of antioxidants and emollients.

Cosmetic compositions for application onto human skin are known in various forms and consistencies, ranging from sprayable fluids which are lighter than water, to solids, such as deodorant sticks. Cosmetic compositions which are typically used in stick-type deodorants contain compounds which are bacterio-static and which are dispersed in a solidified gel. Generally, deodorant stick gels are alcohol-based and contain either propylene glycol or ethanol, and are solidified by the use of a gelling agent, such as a stearate. Some known antiperspirant sticks, however, do not contain any volatile ingredients.

One known antiperspirant stick, which utilizes a combination of waxes of varying melting temperatures to achieve a desired drage, is described in U.S. Pat. No. 4,049,792. In this known antiperspirant stick, a low melting point wax can be used in combination with a high melting point wax to provide a desired mechanical structure and to serve as an emollient. As discussed in this reference, the blending of various high melting point and low melting point waxes can produce a product which feels more brittle, soft, slippery, sticky, rough, etc., to the user. The combining of waxes in this reference does not suggest the cosmetic composition of the present invention, which will be described hereinbelow.

Solid cosmetic compositions are also used for perfume sticks, sun screen sticks, hand lotion sticks, talc sticks, insect repellant sticks, and pigmented sticks, such as lipstick, blushes, or eye shadow. However, most of the known cosmetic compositions which are marketed in the form of cosmetic sticks are designed for easy application and to have a smooth and slippery feel. Most cosmetic sticks presently being marketed have a coefficient of friction on the order of 0.37. One such cosmetic stick has a coefficient of friction of 0.46. None of the known sticks have a coefficient of friction which exceeds 0.5.

It is, therefore, an object of this invention to provide a cosmetic composition which, when apppplied to the skin, has a coefficient of friction of at least 0.5.

It is another object to provide a cosmetic stick which can be applied to the body, particularly the neck, to vigorously massage the skin.

It is a further object to provide a massaging cosmetic stick which can also supply high quality emollients, healing agents, moisturizers, and vitamins.

It is yet a further object to provide a cosmetic stick for massaging action which leaves a non-greasy matte feeling upon application.

It is yet another object of this invention to provide a cosmetic composition consisting of water-in-oil-emulsion, the emulsion having a coefficient of friction of at least 0.5.

It is still yet a further object of this invention to provide a nonaqueous cosmetic composition having a coefficient of friction of at least 0.5.

It is also an object of this invention to provide a cosmetic composition which utilizes acetylated monoglyceride as a major component thereof.

It is additionally an object of this invention to provide a method of preparing a water-in-oil emulsion which, when solidified, exhibits a coefficient of friction of at least 0.5.

It is still another object of this invention to provide a method of preparing a nonaqueous cosmetic composition having a coefficient of friction of at least 0.5.

DESCRIPTION OF THE INVENTION

The foregoing and other objects are achieved by this invention which provides a cosmetic composition of the type which is formable into a cosmetic stick for applying the cosmetic composition to human skin. In accordance with the invention, the cosmetic composition contains approximately between 9.5 and 57% by weight of acetylated monogylceride which has a consistency of a waxy solid. The cosmetic composition further contains between approximately 5 and 39% by weight of beeswax and approximately between 2 and 24% by weight of isopropyl myristate in liquid form and having an emollient characteristic.

In accordance with a method aspect of the invention, an aqueous phase of the compostion is heated to a temperature of approximately 160 degrees F. A fat phase of the cosmetic composition is also heated to a temperature of 160 degrees F., such heating being performed while the phases are mixed vigorously. Subsequently, the aqueous phase is added to the fat phase and mixed vigorously for approximately 10 minutes while the temperature is held at approximately 160 degrees F. In one embodiment of the invention, a coloring compound, such as titanium dioxide, and a fragrance, are added to the heated emulsion while the vigorous mixing is continued. After such mixing, the mixture is permitted to cool to 140 degrees F., and upon reaching this temperature, the emulsion is poured into a container having a predetermined configuration where it is permitted to cool to room temperature. During such cooling, the emulsion is solidified and, upon application to human skin, exhibits a coefficient of friction of at least 0.5.

In accordance with a further method aspect of the invention, a nonaqueous combination of ingredients is heated to 160 degrees F. and mixed for approximately 10 minutes. During such mixing, a fragrance is added, and the composition is subsequently permitted to cool to approximately 140 degrees F. to 145 degrees F. At a preselected temperature in this range, the cosmetic composition is poured into a container having a predetermined configuration where the composition is cooled to room temperature. Upon application to human skin, the resulting cosmetic composition will have a coefficient of friction of at least 0.5.

In a preferred embodiment of the invention, the present cosmetic stick has dispersed therein a synergistic combination of antioxidant compounds. Preferably, one such synergistic component is vitamin E(dl-alpha-tocopherol). Vitamin E is widely used in cosmetic creams and lotions. The second synergistic component is ascorbyl palmitate (the palmitic acid of Vitamin C) is useful as a preservative for the natural oils, oleates, fragrances, colors, vitamins, and other edible oils and waxes which are used in pharmaceuticals, cosmetics, and foods. When used in combination with vitamin E, ascorbyl palmitate performs synergistically with any other antioxidant, particularly in animal fats. The enhanced antioxidation characteristic of the combination of vitamin E with ascorbyl palmitate is believed to reduce the rate of aging of human skin.

A particularly advantageous utilization of the cosmetic composition of the present invention is in the form of a stick which can be used to massage the human body. The high friction characteristic of the composition is particularly suited for massaging the neck area of the body while simultaneously applying emollients or other medicaments.

As used in this disclosure, the coefficient of friction corresponds to a ratio of forces whereby the force required to displace a composition horizontally across a simulated skin surface is compared to the weight, or force, urging the material under test toward the simulated skin surface. In this disclosure, a kinetic coefficient of fricition is more significant than a static coefficient of friction, and therefore, the force required for moving the compound across the simulated skin surface is measured while the composition is moved ten centimeters in twenty seconds.

It has been learned that there is substantially direct correlation between the kinetic coefficient of friction of the compounds and its liquid-to solid ratio. As the liquid: solid ratio decreases, for various compositions, the kinetic coefficient of friction increases.

In one highly advantageous, nonaqueous composition embodiment of the invention, approximately 9.5-57% by weight, and more specifically 43.9% by weight in this specific illustrative embodiment, of distilled acetylated monoglyceride, having the consistency of a waxy solid and a melting temperature of approximately between 105 to 114 degrees F., is utilized as a moisturizer. Between approximately 5 and 39% by weight of the total composition, and specifically 27.3% by weight in this embodiment of beeswax in a solid form having a melting temperature of approximately 149 degrees F., is combined with the acetylated monoglyceride for producing hardness of the composition. The acetylated monoglyceride may be of the type which is marketed under the trademark MYVACET which is owned by Eastman Kodak, Kingsport, TN. To this combination is added between approximately 2 and 24% by weight, and specifically 7.3% by weight in this embodiment, of isopropyl myristate which is available in liquid form and serves as an emollient.

In a further embodiment of the invention, moisturizers may be included in the cosmetic composition which moisturizers may include approximately 2.9% by weight of lanolin in a semisolid form having a melting temperature of approximately between 100 and 108 degrees F.; approximately between 1.5 and 20% by weight, of stearic acid in solid form having a melting temperature of 158 degree F.; and approximately between 1.5 and 18.4% by weight of cetyl alcohol in solid form having a melting temperature of approximately 120 degrees F. In the specific illustrative embodiment, the stearic acid and the cetyl alcohol moisturizers may be contained in amounts of 2.9% by weight each. These may be combined with a liquid emollient such as propylene glycol dicaprylate dicaprate, available under the trademark NEOBEE M20 PVO International, Inc. Boonton, N.J., in a concentration of approximately 1.5% by weight.

Solid emulsifiers such as glycerol monostearate having a melting temperature of approximately 118 degrees F. and marketed under the trademark ARLACEL 165 which is owned by Glyco Chemicals, Inc. of Greenwich, Conn.; and propylene glycol monostearate having a melting temperature of 108 degrees F. Such emulsifiers are present in the specific illustrative embodiment in concentrations of approximately 2.2% by weight.

The specific illustrative cosmetic composition is provided with a preservative, such as methyl/propyl paraben, and a color, such as titanium dioxide, each in concentrations of approximately 0.4% by weight.

In one highly advantageous embodiment of the invention, dry skin is treated by providing approximately 0.1% by weight of vitamin A palmitate. A youthful appearance of the skin is promoted by the synergistic combination of antioxidants, specifically vitamin E (dl-alpha-tocopherol and ascorbyl palmitate). The synergistic antioxidants are present in concentrations of approximately 0.1% by weight each. Additionally, a fragrance is optionally provided.

In another preferred embodiment, a liquid silicone fluid, such as dimethicone or cyclomethicone, of about 3.5 to 8.2% by weight can be added as a sunscreen and emollient.

In the specific illustrative embodiment described hereinabove, the nonpolar liquid:solid ratio is approximately 0.17, and results in a solid cosmetic composition which exhibits a coefficient of friction of 0.83. As previously indicated, the coefficient of friction is determined as a ratio of the magnitude of force required to translate the cosmetic composition across the skin divided by the magnitude of force urging the compostion into communication with the skin.

The tables presented below lists the percentages by weight of the various components in various aqueous and nonaqueous embodiments of the invention. The various embodiments each have respective nonpolar liquid:solid ratios and coefficients of friction. It is interesting to note that the ratios and coefficients nearly linear correlation with each other.

The following table presents various examples of the inventive cosmetic composition, the examples being identified as A to G. Examples A to D are of the aqueous type and contain glycerine as a skin softener, propylene glycol as a humectant, and urea, to impart a healing characteristic to the composition.

Examples E, F and G, each correspond to nonaqueous embodiments, and therefore do not contain water, glycerine, propylene glycol or urea.

In accordance with a method aspect of the invention for producing an aqueous cosmetic composition, the aqueous phase of the composition is heated to a temperature of approximately 160 degrees F. Similarly, the fat phase is heated to a temperature of 160 degrees F., each such phase being mixed vigorously. The aqueous phase is then added to the fat phase to form an emulsion. The emulsion is maintained at the temperature of 160 degrees F. and mixed vigorously for approximately ten minutes. Subsequently, the heated and mixed aqueous and fat phases are cooled to a temperature of 140 degrees F. and poured, at this temperature, into a container having a predetermined configuration, such as a cylinder. If a fragrance is desired, the fragrance, and optionally a color component, is added while the emulsion is being mixed at 160 degrees F.

In accordance with a further aspect method of the invention, a nonaqueous cosmetic composition is produced by combining plurality of ingredients, such as those included in example E, F and G in the table herein. The mixture is heated to a temperature of approximately 160 degrees F. and mixed vigorously. Subsequently, the mixture is cooled to a temperature of approximately between 140 and 145 degrees F. The composition of example G is poured into a container at 145 degrees F., while the compositions of examples E and F are poured at 140 degrees F. Prior to cooling to the temperature range of between 140 and 145 degrees F., a fragrance may optionally be added.

The various ingredients and their proportions used in the foregoing method aspects of the invention are summarized in the following table:

| COMPONENTS | AQUEOUS COMPOSITIONS | | | |
|---|---|---|---|---|
| | A | B | C | D |
| water | 11.7 | 12.1 | 11.6 | 11.4 |
| glycerine | 5.9 | 6.0 | 5.8 | 5.7 |
| propylene glycol | 11.7 | 12.1 | 11.6 | 11.4 |
| urea | 2.3 | 2.4 | 2.0 | 2.3 |
| isopropyl myristate | 11.7 | 6.0 | 8.1 | 8.0 |
| isopropyl palmitate | 5.8 | 2.4 | 3.5 | 3.4 |
| NEOBEE M20 | 1.2 | 0.6 | 1.2 | 1.1 |
| Dimethicone | 2.3 | 1.2 | 1.2 | — |
| Cyclomethicone | — | — | — | — |
| Petrolatum | 1.2 | 0.6 | 0.6 | 0.6 |
| MYVACET | 18.8 | 28.9 | 27.8 | 27.4 |
| Beeswax | 11.8 | 15.4 | 15.0 | 14.8 |
| Stearic acid | 3.5 | 3.6 | 3.5 | 3.6 |
| Cetyl alcohol | 3.5 | 3.6 | 3.5 | 3.4 |
| ARLACEL 165 | 4.2 | 2.6 | 2.1 | 2.1 |
| Propyleneglycol Monostearate | 3.7 | 1.9 | 1.9 | 1.8 |
| methyl/propyl paraben (5:1) preservative | 0.3 | 0.3 | 0.3 | 0.3 |
| Titanium dioxide (Kowet) | 0.— | 0.1 | — | 0.1 |
| Vitamin A palmitate | 0.1 | 0.1 | 0.1 | 0.1 |
| Vitamin E | 0.1 | 0.1 | 0.1 | 0.1 |
| Ascorbyl palmitate | 0.1 | 0.1 | 0.1 | 0.1 |
| Fragrance | Q.S. | Q.S. | Q.S. | Q.S. |
| nonpolar liquid/solid ratio | 0.45 | 0.18 | 0.26 | 0.28 |
| coefficient of friction | 0.59 | 0.82 | 0.75 | 0.67 |

| COMPONENTS | NONAQUEOUS COMPOSITIONS | | |
|---|---|---|---|
| | E | F | G |
| isopropyl myristate | 7.5 | 7.3 | 4.0 |
| NEOBEE M20 | 1.7 | 1.5 | 1.0 |
| Cyclomethicone | 5.8 | 5.8 | 1.0 |
| Lanolin | 2.8 | 2.9 | — |
| Petrolatum | — | — | 1.0 |
| MYVACET | 43.8 | 43.9 | 30.0 |
| Beeswax | 29.0 | 27.3 | 20.0 |
| Stearic acid | 4.2 | 2.9 | 14.3 |
| Cetyl alcohol | 4.2 | 2.9 | 13.2 |
| ARLACEL 165 | — | 2.2 | — |
| LIPOPEG 6000-DS | — | — | 10.3 |
| Propyleneglycol monostearate | — | 2.2 | 4.0 |
| methyl/propyl paraben (5:1) preservative | 0.3 | 0.4 | 0.5 |
| Titanium dioxide (Atlas White) | 0.4 | 0.4 | 0.4 |
| Vitamin A palmitate | 0.1 | 0.1 | 0.1 |
| Vitamin E | 0.1 | 0.1 | 0.1 |
| Ascorbyl palmitate | 0.1 | 0.1 | 0.1 |
| Fragrance | Q.S. | Q.S. | Q.S. |
| nonpolar liquid/solid ratio | 0.18 | 0.17 | 0.06 |
| coefficient of friction | 0.93 | 0.83 | 1.04 |

Approximate Ranges of Concentrations (Percent by Weight of The Illustrative Embodiments)

| COMPONENTS | AQUEOUS | NONAQUEOUS | OVERALL |
|---|---|---|---|
| water | 5.7-12.5 | 0 | 0-12.5 |
| glycerine | 2.8-6.7 | 0 | 0-6.7 |
| propylene glycol | 5.7-12.5 | 0 | 0-12.5 |
| urea | 0-2.6 | 0 | 0-2.6 |
| isopropyl myristate N.P. liquid | 4-14.6 | 2-9.3 | 2-15.6 |
| isopropyl palmitate N.P. liquid | 1.2-7.5 | 0 | 0-13.7 |
| NIOBEE M20 propylene glycol-dicaprylate dicaprate N.P. liquid | 0.3-1.6 | 0.5-2.1 | 0.3-2.25 |
| Dimethicone (Dow 200 silicone fluid) | 0-3.5 | 0 | 0-3.5 |
| Cyclomethicone (Dow 344 silicone fluid) N.P. liquid | 0-3.5 | 0.5-8.2 | 0-8.2 |
| Lanolin - M.P. 100-108F, N.P. semi-solid | 0 | 0-3 | 0-3 |
| Petrolatum - M.P. 100-129F, N.P. semi-solid | 0.3-2.7 | 0-1.5 | 0-2.7 |
| MYVACET (distilled acetylated monoglyceride) M.P. 105-114F N.P. solid | 9.4-34 | 15-51 | 9.5-57 |
| Beeswax - M.P. 149F, N.P. solid | 6-17.2 | 10-34 | 5-38.5 |
| Stearic acid - M.P. 158F N.P. solid | 1.8-4.5 | 1.4-20 | 1.5-20 |
| Cetylalcohol - M.P. 120F-N.P. solid | 1.7-4.6 | 1.4-18.4 | 1.5-18.4 |
| ARLACEL 165 (glycerol monostearate) M.P. 118F | 1-5.3 | 0-3.3 | 0-5.3 |
| LIPOPEG 6000-DS (PEG 150 Distearate) M.P. 110F | 0 | 0-15.5 | 0-15.5 |
| Propylene glycol monostearate-M.P. 108F, N.P. solid | 0.9-4.7 | 0-6 | 0-6 |
| Methyl/propyl paraben (5:1) preservative | 0.1-0.4 | 0.1-0.6 | 0.1-0.6 |
| Titanium dioxide (Korvet) | 0-0.15 | 0 | 0-0.15 |
| Titanium dioxide (Atlas White) | 0 | 0.2-0.6 | 0-0.6 |
| Vitamin A palmitate | 0-0.15 | 0-0.15 | 0-0.15 |
| Vitamin E | 0-0.15 | 0-0.15 | 0-0.15 |
| Ascorbyl palmitate | 0-0.15 | 0-0.15 | 0-0.15 |
| Fragrance | Q.S. | Q.S. | Q.S. |

Although the invention has been described in terms of specific embodiments and applications, persons skilled in the art, in light of this teaching, can generate additional embodiments without exceeding the scope of departing from the spirit of the claimed invention. Accordingly, it is to be understood that the descriptions in this disclosure are preferred to facilitate comprehension of the invention and should not be construed to limit the scope thereof.

What is claimed is:

1. A cosmetic stick composition for applying a cosmetic to human skin, and when applied to the skin has a frictional drag which produces a massaging action, the cosmetic composition consisting essentially of:
approximately between 9.5 and 57% by weight of acetylated monoglyceride having the consistency of a waxy solid; approximately between 5 and 39% by weight beeswax having a melting temperature of approximately 149 degrees F.; and approximately between 2 and 24% by weight of isopropyl myristate in liquid form, and a cosmetic additive selected from the group consisting of pigments, fragrances, antioxidants, emollients, sunscreens, vitamins, humectants, and moisturizers whereby the cosmetic composition has a coefficient of friction which is greater than approximately 0.5.

2. The cosmetic composition of claim 1 wherein there is further provided approximately between 1.5 and 20% by weight of stearic acid having a melting temperature of approximately 158 degrees F.

3. The cosmetic composition of claim 1 wherein there is further provided approximately between 1.5 and 18.4% by weight of cetyl alcohol having a melting temperature of approximately 120 degrees F.

4. The cosmetic composition of claim 1 wherein there is further provided approximately between 0.3 and 2.25% by weight propylene glycol in liquid form.

5. The cosmetic composition of claim 1 wherein there is further provided approximately 0.5 and 8.2% by weight of a silicone in liquid form.

6. The cosmetic composition of claim 1 wherein there is further provided approximately between 0.1 and 0.6% by weight of methyl/propyl paraben in a combination of approximately 5:1.

7. The cosmetic composition of claim 1 wherein there is further provided approximately between 0.2 and 0.6% by weight of titanium dioxide as a coloring agent.

8. The cosmetic composition of claim 1 wherein there is further provided approximately between 0.05 and 0.15% by weight of a selectable combination of vitamin E in the form of Dl-alpha-tocopherol and vitamin C in the form of ascorbyl palmitate.

9. The cosmetic composition of claim 1 wherein there is further provided approximately between 0.5 and 0.15% by weight of vitamin A in the form of palmitate for treating dry skin.

10. The cosmetic composition of claim 1 wherein there is further provided approximately 2.85% by weight of lanolin in a semi-solid form having a melting temperature of approximately between 100 and 108 degrees F.

11. The cosmetic composition of claim 1 wherein there is further provided approximately 10.3% by weight of PEG-150 distearate as a solid emulsifier.

12. The cosmetic composition of claim 1 wherein there is further provided approximately between 5.7 and 16.5% by weight of water.

13. The cosmetic composition of claim 12 wherein there is further provided approximately between 2.3 and 6.7% by weight of glycerine for providing skin softening properties to the cosmetic composition.

14. The cosmetic composition of claim 12 wherein there is further provided approximately between 2.4 and 15.7% by weight of propylene glycol as a humectant.

15. The cosmetic composition of claim 12 wherein there is further provided approximately between 1.0 and 3.1% by weight of urea for providing healing properties to the cosmetic composition.

16. The cosmetic composition of claim 12 wherein there is further provided approximately between 1.2 and 13.7% by weight of isopropyl palmitate in liquid form as an emollient.

17. The cosmetic composition of claim 12 wherein there is further provided approximately between 1.1 and 5.25% by weight of glycerol monostearate in the form of a solid having a melting temperature of approximately 118 degrees F., as an emulsifier.

18. A cosmetic stick composition for applying a cosmetic to human skin, and when applied to the skin has a frictional drag which produces a massaging action, the cosmetic composition consisting essentially of:

approximately between 9.5 and 57% weight of acetylated monoglyceride having the consistency of a waxy solid; approximately between 5 and 39% by weight beeswax having a melting temperature of approximately 149 degrees F.;

approximately between 2 and 24% by weight of isopropyl myristate in liquid form;

approximately between 1.5 and 20% by weight of stearic acid having a melting temperature of approximately 158 degrees F.;

approximately between 1.5 and 18.4% by weight of cetyl alcohol having a melting temperature of approximately 120 degrees F.;

approximately between 0.3 and 2.25% by weight propylene glycol in liquid form;

approximately between 0.1 and 0.6% by weight of methyl/propyl paraben in a combination of approximately 5.1;

approximately between 0.2 and 0.6% by weight of methyl/propyl paraben in a combination of approximately 5.1;

approximately between 0.2 and 0.6% by weight of titanium dioxide as a coloring agent; and a cosmetic additive selective from the group consisting of pigments, fragrances, antioxidants, emollients, sunscreens, vitamins, humectants, and moisturizers and whereby the cosmetic composition has a coefficient of friction which is greater than approximtely 0.5.

19. A method of preparing a cosmetic stick, the method of comprising the steps of:

combining a plurality of ingredients selected from a group comprised of acetylated monoglyceride, beeswax, stearic acid, distearate, isopropyl myristate, propylene glycol monostearate, a color component, cetyl alcohol, cyclomethicone lanolin and an antioxidant, in predetermined proportions to form a mixture;

heating said mixture to a temperature of 160 degrees F.;

mixing said mixture during said step of heating;

cooling said mixture to a predetermined temperature approximately between 140 and 145 degrees F.;

pouring said mixed, cooled mixture into a container having a stick configuration; and further cooling the cosmetic composition in said container whereby said further cooled cosmetic composition has a coefficient of friction of at least 0.5.

* * * * *